US00PP13114P2

(12) United States Plant Patent
Cornelis

(10) Patent No.: US PP13,114 P2
(45) Date of Patent: Oct. 22, 2002

(54) SPATHIPHYLLUM PLANT NAMED 'PICCOLINO II'

(75) Inventor: Daniel Cornelis, Merelbeke-Melsen (BE)

(73) Assignee: Milestone Agriculture, Inc., Apopka, FL (US)

( * ) Notice: Subject to any disclaimer, the term of this patent is extended or adjusted under 35 U.S.C. 154(b) by 0 days.

(21) Appl. No.: 09/561,016

(22) Filed: Apr. 28, 2000

(51) Int. Cl.[7] ..... A01H 5/00

(52) U.S. Cl. ..... Plt./364

(58) Field of Search ..... Plt./364

(56) References Cited

PUBLICATIONS

Henny et al.; Spathiphyllum Cultivars Vary in Flowering Response after Treatment with Gibberellic Acid; HortTechnology, vol. 9(2), Abstract, 1999.*
GTITM UPOVROM Citation for 'Piccolino' as per QZ PBR 971225; Sep. 29, 1997.*

* cited by examiner

*Primary Examiner*—Kent L. Bell
(74) *Attorney, Agent, or Firm*—C. A. Whealy

(57) ABSTRACT

A distinct cultivar of Spathiphyllum plant named 'Piccolino II', characterized by its very compact plant habit; dark green, shiny leaves; very freely clumping, dense and bushy plants; freely flowering; numerous white spathes that are positioned at or above the foliage on strong and erect peduncles and long-lasting spathes.

1 Drawing Sheet

BOTANICAL CLASSIFICATION/CULTIVAR DESIGNATION

*Spathiphyllum Schott.* cultivar 'Piccolino II'.

BACKGROUND OF THE INVENTION

The present Invention relates to a new and distinct cultivar of Spathiphyllum plant, botanically known as *Spathiphyllum Schott.*, and hereinafter referred to by the cultivar name 'Piccolino II'.

The new cultivar is a product of a planned and controlled breeding program conducted by the Inventor in Merelbeke-Melsen, Belgium. The objective of the breeding program is to create compact and freely-flowering Spathiphyllum cultivars suitable for 10-cm production with dark green leaves. The new cultivar originated from a deliberate cross by the Inventor in 1997 between the Spathiphyllum cultivar 'Jungfrau', disclosed in U.S. Plant Pat. No. 10,627, as the female or seed parent and the Spathiphyllum cultivar 'Daniel', disclosed in U.S. Plant Pat. No. 8,655, as the male or pollen parent. The cultivar 'Piccolino II' was discovered and selected by the Inventor as a plant within the progeny of the stated cross in a controlled environment in Merelbeke-Melsen, Belgium.

Compared to plants of the female parent, the cultivar 'Jungfrau', plants of the new Spathiphyllum are more compact, have darker green leaves and larger spathes and spadices. Compared to plants of the male parent, 'Daniel', plants of the new Spathiphyllum are more compact and have darker green leaves.

Plants of the new Spathiphyllum differ from plants of the cultivar 'Piccolino', not patented, primarily in plant growth habit.

Asexual propagation of the new cultivar by tissue culture in a laboratory in Belgium has shown that the unique features of this new Spathiphyllum plant are stable and reproduced true to type in successive generations of asexual propagation.

SUMMARY OF THE INVENTION

The new Spathiphyllum has not been observed under all possible environmental conditions. The phenotype may vary somewhat with variations in environment such as temperature, light intensity, fertilizer level and propagation procedures, without, however, any variance in genotype.

The following traits have been repeatedly observed and are determined to be the unique characteristics of 'Piccolino II'. These characteristics in combination distinguish 'Piccolino II' as a new and distinct cultivar:

1. Very compact plant habit.
2. Dark green, shiny leaves.
3. Very freely clumping, dense and bushy plants.
4. Freely flowering.
5. Numerous white spathes that are positioned at or above the foliage on strong and erect peduncles.
6. Long-lasting spathes.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new Spathiphyllum.

The photograph comprises a side perspective view of a typical plant of 'Piccolino II' in a 10-cm container.

DETAILED BOTANICAL DESCRIPTION

The following observations, measurements and comparisons describe 20-week old plants (from microcuttings) grown in Apopka, Fla., during the spring, under commercial greenhouse conditions in 10-cm containers. Day temperatures ranged from 24 to 32° C. and night temperatures ranged from 18 to 24° C. Light level was about 1,500 foot-candles.

In the following description, color references are made to The Royal Horticultural Society Colour Chart except where general terms of ordinary dictionary significance are used.

Parentage:

*Female or seed parent.*—Spathiphyllum cultivar 'Jungfrau', disclosed in U.S. Plant Pat. No. 10,627.

*Male or pollen parent.*—Spathiphyllum cultivar 'Daniel', disclosed in U.S. Plant Pat. No. 8,655.

Propagation:

*Type.*—By tissue culture.

*Time to initiate roots.*—Summer: About 30 days at 24° C. Winter: About 45 days at 21° C.

*Time to develop roots.*—Summer: About 70 days at 24° C. Winter: About 80 days at 21° C.

*Root description.*—Freely branching, numerous fleshy roots.

Plant description:

*Plant shape.*—Upright, inverted triangle, symmetrical.

*Growth habit.*—Erect when young, becoming outwardly arching to drooping as leaves develop. Freely clumping with numerous new shoots; full and bushy appearance. Very compact, appropriate for 10-cm containers.

*Plant height.*—About 27 cm from soil level to top of leaf plane.

*Plant spread.*—About 37 cm.

*Plant vigor.*—Moderately vigorous.

*Crop time.*—About 20 weeks are required to produce a finished flowering plant in 10-cm container from a tissue-cultured microcutting.

*Foliage description.*—Length: About 22 cm. Width: About 8.3 cm. Shape: Roughly oblong. Apex: Elongated acuminate. Base: Cuneate. Margin: Entire; undulate. Aspect: Initially upright, then reflexed. Surface: Rugose; undulating. Texture: Leathery, smooth, glabrous, very durable; flexible; both surfaces glossy. Color: Young, upper surface: Darker than 146A. Young, lower surface: Greener than 146A. Mature, upper surface: Close to 147A. Mature, lower surface: Close to 147B. Petiole length, primary shoots: About 17.5 cm. Petiole diameter, base: About 7.5 mm. Petiole diameter, above geniculum: About 3 mm. Strength: Strong, flexible. Color: Below geniculum, 146A; geniculum and above geniculum, close to 144A. Wing length: About 14.5 cm. Wing diameter: About 6 mm. Geniculum length, primary shoots: About 7 mm. Geniculum diameter, primary shoots: About 4 mm.

Inflorescence description:

*Inflorescence arrangement.*—Concave spathes with spadices held above the foliage. Freely flowering; numerous inflorescences arise from leaf axils, typically about three to six per plant. Not fragrant.

*Inflorescence longevity.*—Inflorescences are long-lasting, generally maintaining white color for about two or three months on the plant depending on light and temperature levels.

*Spathe.*—Length: About 8 cm. Width: About 3.9 cm. Shape: Ovate. Apex: Elongated acuminate. Base: Cuneate to obtuse. Aspect: Concave, curling over the spadix. Color, both surfaces: White, 155A, becoming green, 144A, with development.

*Spadix.*—Length: About 3.2 cm. Diameter: About 1.1 cm. Number of flowers per spadix: More than 50. Color: 158D becoming green, 144A, with development. Pollen: White, close to 155A.

*Peduncle.*—Aspect: Strong and erect. Length: About 24 cm. Diameter: About 3 mm. Color: Close to 144A.

*Seed.*—Seed development has not been observed.

Disease resistance: Plants of the new Spathiphyllum have exhibited good resistance to pathogens common to Spathiphyllum.

Temperature tolerance: Plants of the new Spathiphyllum have been shown to tolerate temperatures from 6 to 37° C.

It is claimed:

1. A new and distinct cultivar of Spathiphyllum plant named 'Piccolino II', as illustrated and described.

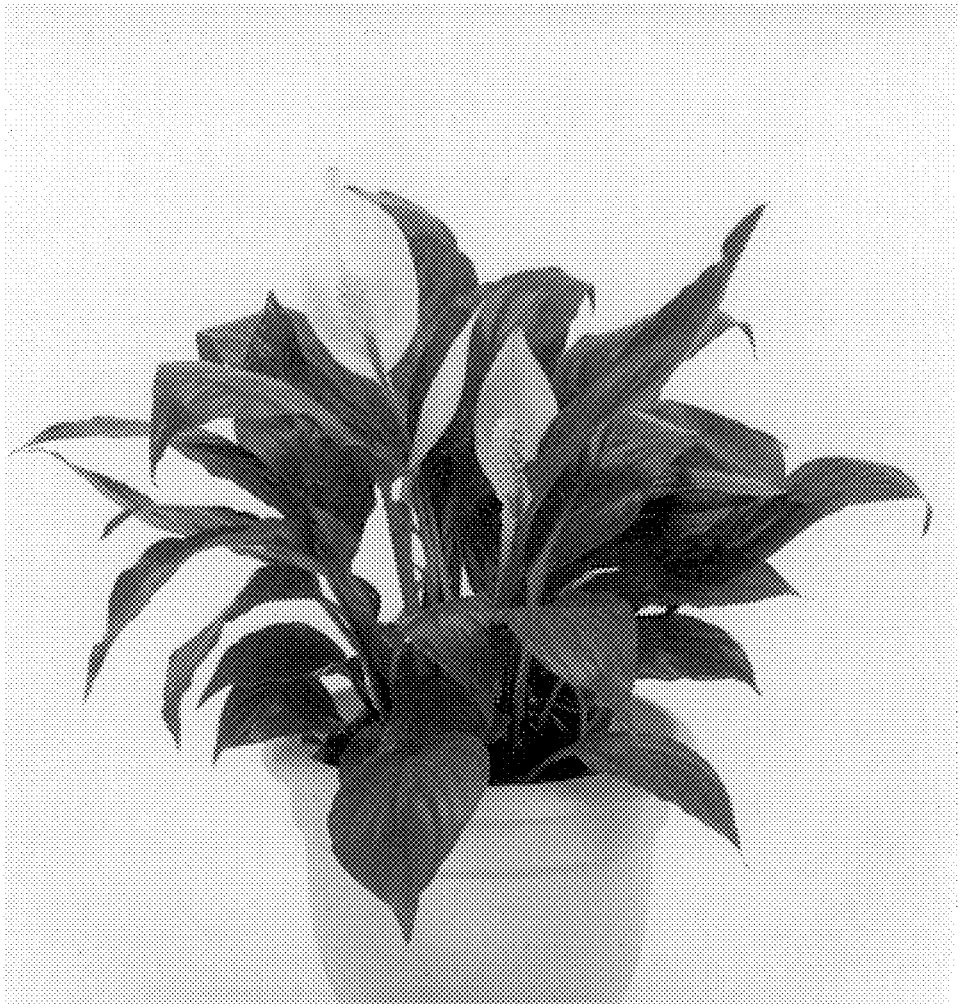

* * * * *